United States Patent [19]

Masuhara et al.

[11] Patent Number: 4,484,894
[45] Date of Patent: Nov. 27, 1984

[54] SHEET FOR LINING DENTURE BASE

[75] Inventors: Eiichi Masuhara, 2-5-10 Hon-Komagome, Bunkyo-ku, Tokyo, Japan; Kunizoh Kidoh; Nobuo Bannai, both of Iwaki, Japan

[73] Assignees: Eiichi Masuhara; Kureha Kagaku Kagaku Kogyo Kabushiki Kaisha, both of Tokyo, Japan

[21] Appl. No.: 351,467

[22] Filed: Feb. 23, 1982

Related U.S. Application Data

[63] Continuation-in-part of Ser. No. 183,733, Sep. 3, 1980, abandoned, which is a continuation-in-part of Ser. No. 61,244, Jul. 27, 1979, abandoned.

[51] Int. Cl.³ .............................. A61C 13/02
[52] U.S. Cl. .................................... 433/168
[58] Field of Search ................... 433/217, 168

[56] References Cited

U.S. PATENT DOCUMENTS

| | | | |
|---|---|---|---|
| 3,030,260 | 4/1962 | Metzler et al. | 156/305 |
| 3,449,305 | 6/1969 | Stilmar | 428/421 X |
| 3,839,743 | 10/1974 | Schwarcz | 433/168 |
| 3,889,374 | 6/1975 | Saffir | 433/199 |
| 4,029,868 | 6/1977 | Carlson | 526/247 |
| 4,123,603 | 10/1978 | Steuard, Jr. | 433/168 |

FOREIGN PATENT DOCUMENTS

| | | | |
|---|---|---|---|
| 6850 | 6/1966 | Australia . | |
| 67601 | 4/1974 | Australia . | |
| 932100 | 8/1973 | Canada . | |
| 923451 | 2/1955 | Fed. Rep. of Germany . | |
| 1108025 | 1/1956 | France . | |
| 2222066 | 2/1974 | France | 433/168 |
| 739988 | 11/1955 | United Kingdom | 433/168 |
| 982814 | 5/1965 | United Kingdom . | |
| 1441287 | 6/1976 | United Kingdom . | |
| 1496084 | 12/1977 | United Kingdom . | |
| 1504048 | 3/1978 | United Kingdom . | |
| 1515799 | 6/1978 | United Kingdom . | |
| 2027043 | 8/1978 | United Kingdom | 433/168 |

Primary Examiner—Robert Peshock
Attorney, Agent, or Firm—Wegner & Bretschneider

[57] ABSTRACT

Disclosed herein are sheet for lining denture base prepared by molding a copolymer consisting of vinylidene fluoride units, tetrafluoroethylene units, hexafluoropropylene units and/or chlorotrifluoroethylene units in their mutual ratio within a predetermined range into shapes of sheets.

2 Claims, 1 Drawing Figure

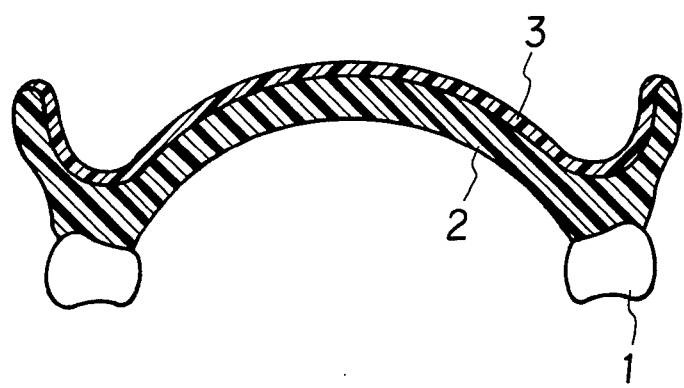

SHEET FOR LINING DENTURE BASE

CROSS-REFERENCE OF RELATED APPLICATION

The present application is a continuation-in-part of application Ser. No. 183,733 and now abandoned, filed on Sept. 3, 1980 which is a continuation-in-part of application Ser. No. 61,244, filed on July 27, 1979 and now abandoned.

SUMMARY OF THE INVENTION

In an aspect of the present invention, there is provided a sheet for lining a denture base substantially made of polymethyl methacrylate, comprising a copolymer consisting of 40 to 60 parts by weight of vinylidene fluoride units, 20 to 30 parts by weight of tetrafluoroethylene units and 20 to 30 parts by weight of hexafluoropropylene units and/or chlorotrifluoroethylene units, of 0.2 to 3.0 mm in thickness and having a modulus of rigidity of 5 to 200 kg/cm$^2$.

BACKGROUND OF THE INVENTION

The present invention relates to sheets for lining denture base.

The "lining denture base" is the abbreviated expression indicating the material which lines one of the surfaces of a dental base, particularly the surface which faces to the gingival- and palatal surface in the mouth.

Hitherto, resins derived from methacrylates have been used for manufacturing denture base. However, in the cases where the absorption by the alveolar arch is strong, there cases where desirable results can not be obtained by the denture base solely made of methacrylate resin. In such cases, there are possibilities of causing pain on the thin gingival mucosa got between the hard denture base and the gingiva, the pain occasionally leading to a kind of ulcer. Consequently it is necessary to line the denture base facing to the gingival mucosa which has come to be thinner by the use of the hard denture base with a material which is able to substitute the lost thickness of the original mucosa which is naturally elastic to a certain extent. The material for lining the surface of the denture base, which faces to the gingival membrane, playing a role of soft cushion is referred to as "soft lining denture base". The major role of the soft lining denture base is to compensate the lost thickness of the mucosa and to relax the impact of mastication as well as to disperse uniformly the masticatory pressure onto the mucosa.

In early days, as the soft material for lining denture base of methacrylate resin, vinyl polymers, copolymer of acrylate esters or one of those added with plasticizers has been applied. However, such a material could not give clinically satisfactory results for a long term because of its substantial instability such as swelling within the mouth due to absorption of moisture, deterioration due to aging and exuding foreign substances. Although a soft lining material for denture bases excellent in elasticity and water-proofness has been developed from derivatives of silicone thereafter, there are still problems to be solved such as insufficiency of adhesion to the resin constituting the denture base, liberation of the generation of bacteria such as Candida and difficulty of polishing the lined surface, etc.

Although methacrylate resin is still in use as the material for the denture base at present, it is preferable that the lining material for the denture base fulfills the following essential conditions:

(1) It is biologically safe for a long term.
(2) It does not deteriorate for a long period within the mouth and does not show any change in its pliability and mechanical properties.
(3) It adheres firmly to the methacrylate resin constituting the denture base without defoliating for a long period within the mouth.
(4) It is free from abrasion within the mouth.
(5) It is easily processable in cutting and polishing to have the smoothly polished surface and
(6) It is easily and conveniently processed by forming and finishing.

Attempts of substituting a fluoropolymer for polymethyl methacrylate of the dental base have been carried out, for instance, in U.S. Pat. No. 3,889,374, however, nothing is disclosed therein concerning the overcoming of the defects of polymethyl methacrylate as the material for lining denture base.

After studying with an intention of providing a material as the lining denture base provided with the specific characteristics, the present inventors have found that sheets prepared from a specified fluorine-containing copolymer are capable of fulfilling the demand for the specific characteristics, and have attained to the present invention.

BRIEF EXPLANATION OF THE DRAWING

The drawing shows the perpendicular cross sectional view of a denture base lined with the lining denture base according to the present invention.

The following is the detailed explanation of the present invention:

DETAILED EXPLANATION OF THE INVENTION

The main characteristics of the present invention resides in that a copolymer consisting of respective units of vinylidene fluoride, tetrafluoroethylene, hexafluoropropylene and/or chlorotrifluoroethylene in their mutual weight ratio within a predetermined range is processed to be shape of sheets. The copolymer is specified by its compositions of 40 to 60 parts by weight of vinylidene fluoride units, 20 to 30 parts by weight of tetrafluoroethylene units, and 20 to 30 parts by weight of hexafluoropropylene units and/or chlorotrifluoroethylene units and its modulus of rigidity of 5 to 200 kg/cm$^2$.

The range of the mutual weight ratio of the respective monomeric units is extremely important for fulfilling the demand for specific characteristics.

In the case where the weight ratio of vinylidene fluoride units is smaller than the range, the adhesion of the sheet for lining denture base to the denture base, for instance, those made of methacrylate resin, is poor, and on the other hand, in the case where the weight ratio is larger than the range, the sheet for lining denture base becomes so large in rigidity that the sheet is not able to mitigate the occlusal pressure loaded on the denture base. In addition, in the case where both of the weight ratio of tetrafluoroethylene units and that of hexafluoropropylene units and/or chlorotrifluoroethylene units are out of the range, the sheet made of such a copolymer cannot afford the necessary rigidity and the creep property to the denture base.

That is, the copolymer forming the sheet for lining denture base according to the present invention should consist of the three kinds of or the four kinds of the monomer units and these units should be in the weight ratio within the range.

In the drawing, 1, 2, and 3 respectively show an artificial tooth, a denture base and a sheet for lining denture base according to the present invention.

The sheet 3 for lining the denture base 2 situates between the denture base 2 and the gingival mucosa in order to play a role of cushioning for the thin gingival mucosa between the denture base 2 and the alveolar bone. The sheet 3 for lining the denture base 2 not only plays a role of cushioning for the gingival mucosa but also functions of compensating the already lost thickness of the gingival mucosa and relaxing the impact caused by mastication and distributing the masticating pressure uniformly onto the surface of the gingival mucosa.

The sheet for lining denture base according to the present invention are prepared by molding the copolymer into shapes of sheets, without adding any additives and preferably have a thickness of 0.2 to 3 mm, more preferably of 0.3 to 2 mm. In the case where the thickness is smaller than 0.2 mm, since its buffering action on the occlusal pressure to the gingival mucoso is small, the purpose of the soft resin lining is not fulfilled. On the other hand, in the case where the thickness is larger than 3 mm, an unpleasant feeling is given to the person who use the denture as if he always was chewing a rubber, because of the large thickness of the lining.

The following table shows the result of determinations of the modulus of rigidity, the adhesion strength to denture base, the water-absorption, the creep property and the presence or absence of any eluated substances by the absorbed water of the sheet for lining denture base according to the present invention, and thus explains the suitability of the sheet for lining denture base. In addition, the result of determination of the corresponding properties of both of the silicone rubber sheet is shown also in the table for comparison.

The determination of the properties was carried out following the methods shown below.

Modulus of rigidity:
"Test for softening temperature" by Japanese Industrial Standard (JIS) K 6745, 7.5.

Strength of adhesion:
Using a specimen prepared by pressing a sheet made of the copolymer under test of 1 mm in thickness onto a sheet of polymethyl methacrylate of 1 mm in thickness as the denture base at a temperature of 150° C. and a pressure of 10 kg/cm$^2$ for 5 min, applied on a shearing tester.

Water absorption:
After immersing a specimen prepared into a sheet of 1 mm in thickness into an artificial saliva at 40° C. for 24 hours, the increment of the weight of the specimen is expressed by %.

Creep property:
The elongation of the specimen prepared to a sheet of 0.7 (thickness)×10 (width)×10 (length) mm, when loaded a known weight at its one end at 24° C.

Presence or absence of eluated substance:
After immersing a specimen prepared to a sheet of 1 mm in thickness into distilled water at pH of 6.6 for 20 days at room temperature, the alteration of pH and the ultraviolet absorption of the water are determined to judge the presence or absence of the eluated substance in the water.

TABLE

| | Properties of Sheets for Lining Denture Base | | | | | | |
|---|---|---|---|---|---|---|---|
| Composition* of copolymer (parts by weight) | Modulus of rigidity | Strength of adhesion (kg/cm$^2$) | % Water absorption (mg/cm$^2$) | Creep property under load of | | Eluation | |
| | | | | 1.0 kg (%/mm$^2$) | 1.2 kg (%/mm$^2$) | pH | P** |
| 1. VF: 60 TF: 20 CT: 20 | 130.0 | 330 | 0.032 | 0 | 19.0 | 6.6 | No |
| 2. VF: 55 TF: 20 CT: 25 | 79.0 | 346 | 0.037 | 0 | 71.2 | 6.6 | No |
| 3. VF: 50 TF: 20 CT: 30 | 88.2 | 360 | 0.040 | 0 | 70.0 | 6.6 | No |
| 4. VF: 45 TF: 25 CT: 30 | 80.0 | 363 | 0.042 | 0 | 61.5 | 6.6 | No |
| 5. VF: 40 TF: 30 CT: 30 | 65.6 | 358 | 0.042 | 0 | 84 | 6.6 | No |
| 6. VF: 45 TF: 25 CT: 15 HF: 15 | 70.7 | 340 | 0.029 | 0 | 75 | 6.6 | No |
| 7. VF: 60 TF: 20 HF: 20 | 88.5 | 325 | 0.020 | 0 | 63 | 6.6 | No |
| 8. Silicone Rubber | 50.3 | 40.5 | 0.33 | 0 | 21 | 5.8 | Yes |

Notes:
(1) Nos. 1 to 7 are according to the present invention, and No. 8 is that for comparison.
(2) *VF: vinylidene fluoride, TF: tetrafluoroethylene, CT: chlorotrifluoroethylene, HF: hexafluoropropylene
(3) **Presence of eluated substance.

As is seen in the Table, the sheet for lining denture base according to the present invention has a superior adhesion to the denture base composed of polymethyl methacrylate as compared to the hitherto utilized silicone rubber for that purpose and in addition, the sheet according to the present invention absorbs far smaller amount of water than the silicone rubber, and still more, the sheet according to the present invention does not form any eluated substance when immersed into water. All these properties contribute to the stability of the sheet for lining denture base according to the present invention within the oral cavity.

The effects of the properties on the function of the sheet for lining denture base are further explained as follows:

The larger strength of adhesion of the sheet for lining denture base makes the utilization of an adhesive unnecessary and so the elution of substance within the oral cavity caused by the use of the adhesive can be avoided. In order not to use any adhesives, the strength of adhesion between the sheet and the denture base is preferably higher than 250 kg/cm$^2$.

On the other hand, the larger creep means the eventual loss of the elasticity of the material forming the lining of denture base by the action of repeatedly loaded occlusal pressure mainly onto the mucosal membrane of the gingiva. The eventual loss of the elasticity causes the loss of cushioning property which is the substantial function of the lining itself. That is, in order to prevent the deterioration of the functional properties of the lining, it is preferable tht the determined value of the creep under the load of 1 kg is substantially zero and the creep value under the load of 1.2 kg is less than 100%.

Further more, as for the amount of water absorbed by the sheet for lining denture base, since the lining of denture base is always used within the oral cavity, the value of absorbed amount of water is the smaller the better, and it is preferably less than 0.05%.

Concerning the rigidity, as has been described before, since the rigidity of the sheet for lining denture base affects the mitigation of the occlusal pressure on the mucous membrane of the gingiva via the denture base and the close adhesion to the mucous membrane of the oral cavity, a rigidity with somewhat softness is demanded, and for that purpose, the value of modulus of rigidity is 5 to 200 kg/cm$^2$, preferably, 10 to 150 kg/cm$^2$.

As has been described, the sheet for lining denture base according to the present invention satisfactorily fulfills the necessary conditions demanded for such a sheet, and accordingly, the sheet is said to be extremely valuable in practical use.

The following is the exemplification of the present invention while referring to Examples which also show the methods of application of the sheet for lining denture base. In thoe Examples, part means part by weight unless specified.

EXAMPLE 1

A pressed sheet of 0.7 mm in thickness was prepared by pressing, at a raised temperature, a copolymer consisting of 60 parts by weight of vinylidene fluoride units, 20 parts by weight of tetrafluoroethylene units and 20 parts by weight of hexafluoropropylene units. The sheet was placed on a surface of a formed soft prepolymer of methyl methacrylate which has been formed in a gypsum mold to be a denture base having the pieces of artificial teeth, the surface being to be in contact with the mucous membrane of the alveolar arch and the sheet of the fluorocopolymer and the formed prepolymer were kept for 30 min. at a temperature of 100° C. while being pressed between the upper and lower molds of gypsum. Owing to the polymerization and solidification of the prepolymer, the soft fluorocopolymer adhered firmly onto the surface of the thus solidified denture base of polymethyl methacrylate. After taking the rough denture from the molds, its shape was retouched and its surface was polished to be a desired denture having its denture base lined with the soft fluorocopolymer. The thus prepared denture was used by a man of 60 year-old for 24 months without any defect and it seemed to be usable for a long time period furthermore.

EXAMPLE 2

A copolymer consisting of 40 parts by weight of vinylidene fluoride units, 30 parts by weight of tetrafluoroethylene units and 30 parts by weight of chlorotrifluoroethylene units was pressed at a high temperature to be a sheet of 0.8 mm in thickness. The thus obtained sheet for denture base lining was applied onto a denture base made of polymethyl methacryrate and had been in actual use for about one year by the following procedures:

The surface facing to the gingival mucosal membrane and partly to alveolar mucosal membrane of the above-mentioned denture base was scraped off about 1 mm in depth for obtaining the fresh surface of polymethyl methacrylate in advance of lining. After burying the denture base in gypsum contained in a flask in accordance with the conventional rebase method, prepolymer of methyl methacrylate in a sticky rice-cake like state was placed on the thus treated surface of the denture base as a layer of about 2 to 3 mm in thickness and a trial molding was carried out. Then, the sheet for lining denture base was placed on the laminate, and a trial molding was once again carried out. In this procedure, the prepolymer in a rice cake-like state played a role of adhering the denture base to the sheet for lining the denture base and of making up of the space between the two. After completing the trial molding, hot water at 80° to 100° C. was poured into the flask under pressure to immerse the prepolymer into the hot water for 30 min at the temperature to be polymerized and solidified. By these procedures, the sheet firmly adhered to the treated surface of the denture base. The thus obtained denture was taken out from the gypsum mold, amended and polished to be the desired denture rebased and lined with the sheet for lining denture base according to the present invention.

EXAMPLE 3

A pressed sheet of 0.8 mm in thickness was prepared by heating and pressing a copolymer comprising 50 parts by weight of vinylidene fluoride units, 30 parts by weight of chlorotrifluoroethylene units and 20 parts by weight of tetrafluoroethylene units. After setting by a pressure the thus prepared sheet onto the surface of a denture base made of a prepolymer of methyl methacrylate facing to the gingival mucous membrane, which has been shaped by pressing with gypsum mold, the whole system consisting of the sheet, the prepolymer and the gypsum mold was heated for 30 min at 100° C., to complete the polymerization of methyl methacrylate. As a result, a denture base of hardened polymethyl methacrylate lined with the strongly adhered sheet of fluorocopolymer on the surface of the denture base, which faces to the gingival mucous membrane. After taking the denture base from the gypsum molding, the shape of the denture base was retouched, and the surface of the denture base was polished to be a completed denture base lined with the sheet of fluorocopolymer.

This and the similarly prepared denture bases were applied on 15 male persons of age of 60 to 70, and at present, after 2 years, no complaint on the abnormality of the denture base has been heard. Also on the examination of these denture bases, it was concluded that these denture bases would be continuously utilizable still longer.

What is claimed is:

1. A cushioning sheet adapted for lining the gingival mucosa-facing surface of a polymethyl methacrylate denture base, said sheet consisting essentially of a copolymer consisting essentially of 40 to 60 parts by weight of vinylidene fluoride units, 20 to 30 parts by weight of tetrafluoroethylene units and 20 to 30 parts by weight of hexafluoropropylene units and/or chlorotrifluoroethylene units, said sheet being 0.2 to 3.0 mm in thickness and having a modulus of rigidity of 10 to 150 kg/cm$^2$, a water absorbance of less than 0.05% and an adhesion strength of more than 250 kg/cm$^2$.

2. A polymethyl methacrylate denture base having its gingival mucosa-facing surface lined with a cushioning sheet, said cushioning sheet consisting essentially of 40 to 60 parts by weight of vinylidene fluoride units, 20 to 30 parts by weight of tetrafluoroethylene units and 20 to 30 parts by weight of hexafluoropropylene units and/or chlorotrifluoroethylene units, said cushioning sheet being 0.2 to 3 mm in thickness and having a modulus of rigidity of 10 to 150 kg/cm$^2$, a water absorbance of less than 0.05% and an adhesion strength of more than 250 kg/cm$^2$.

* * * * *

UNITED STATES PATENT AND TRADEMARK OFFICE
CERTIFICATE OF CORRECTION

PATENT NO. : 4,484,894

DATED : November 27, 1984

INVENTOR(S) : Masuhara et al.

It is certified that error appears in the above-identified patent and that said Letters Patent is hereby corrected as shown below:

Cover sheet at [73] Assignees: amend to read:

--Eiichi Masuhara; Kureha Kagaku Kogyo Kabushiki Kaisha, both of Tokyo, Japan--

Signed and Sealed this

Seventh Day of January 1986

[SEAL]

Attest:

DONALD J. QUIGG

Attesting Officer

Commissioner of Patents and Trademarks